United States Patent
Rosenbaum

[11] Patent Number: 6,050,987
[45] Date of Patent: Apr. 18, 2000

[54] TUBULAR COUPLING

[75] Inventor: Bernard J. Rosenbaum, Seabrook, Tex.

[73] Assignee: The United States of America as represented by the Administrator of the National Aeronautics and Space Administration, Washington, D.C.

[21] Appl. No.: 09/157,759

[22] Filed: Sep. 21, 1998

[51] Int. Cl.[7] .................................................. A61M 25/16
[52] U.S. Cl. ........................ 604/533; 285/248; 604/534; 604/535
[58] Field of Search ................... 604/533–536, 604/905; 285/246, 248, 249

[56] References Cited

U.S. PATENT DOCUMENTS

| | | | |
|---|---|---|---|
| 4,303,263 | 12/1981 | Legris | 285/249 |
| 4,625,712 | 12/1986 | Wampler | 128/1 D |
| 4,908,012 | 3/1990 | Moise et al. | 600/16 |
| 5,061,256 | 10/1991 | Wampler | 128/1 D |
| 5,376,114 | 12/1994 | Jarvik | 623/3 |
| 5,514,117 | 5/1996 | Lynn | 604/283 |
| 5,527,159 | 6/1996 | Bozeman, Jr. et al. | 417/45 |
| 5,599,173 | 2/1997 | Chen et al. | 417/412 |

*Primary Examiner*—Corrine McDermott
*Assistant Examiner*—Eric Kline
*Attorney, Agent, or Firm*—Hardie R. Barr

[57] ABSTRACT

A system for coupling a vascular overflow graft or cannula to a heart pump. A pump pipe outlet is provided with an external tapered surface which receives the end of a compressible cannula. An annular compression ring with a tapered internal bore surface is arranged about the cannula with the tapered internal surface in a facing relationship to the external tapered surface. The angle of inclination of the tapered surfaces is converging such that the spacing between the tapered surfaces decreases from one end of the external tapered surface to the other end thereby providing a clamping action of the tapered surface on a cannula which increases as a function of the length of cannula segment between the tapered surfaces. The annular compression ring is disposed within a tubular locking nut which threadedly couples to the pump and provides a compression force for urging the annular ring onto the cannula between the tapered surfaces. The nut has a threaded connection to the pump body. The threaded coupling to the pump body provides a compression force for the annular ring. The annular ring has an annular enclosure space in which excess cannula material from the compression between the tapered surfaces to "bunch up" in the space and serve as an enlarged annular ring segment to assist holding the cannula in place. The clamped cannula provides a seamless joint connection to the pump pipe outlet where the clamping force is uniformly applied to the cannula because of self alignment of the tapered surfaces. The nut can be easily disconnected to replace the pump if necessary.

6 Claims, 1 Drawing Sheet

TUBULAR COUPLING

ORIGIN OF THE INVENTION

The invention described herein was made by employee(s) of the United States government and may be manufactured and used by and for the Government of the United States of America for governmental purposes without the payment of any royalties thereon or therefor.

FIELD OF THE INVENTION

The present invention relates to an improved system for connecting cannulae with blood pumps and universally useful for coupling a flexible tube to a pipe while providing a seamless interior joint.

PRIOR ART

U.S. Pat. No. 5,527,159, issued Jun. 18, 1996 illustrates an axial flow ventricle assist blood pump which is a device to assist a functioning heart to pump sufficient blood for circulation. No clamping means are shown.

U.S. Pat. No. 5,599,173, issued on Feb. 4, 1997 to Chen et al and assigned to Baxter International Inc., discloses a blood pump for internal use in humans, including a technique for connecting removable inlet and outlet conduits to the inlet and outlet means using concentric seals and a housing ring which is secured to the pump bulkhead. The housing ring includes threads disposed on the outwardly extending flange which are adapted to engage conduit threads. The connector may also include keyed slots to assure appropriate placement of the inlet and outlet valved conduits.

U.S. Pat. No. 5,514,117, issued on May 7, 1996 to Lynn, no assignment noted, discloses an improved universal connector for coupling intravenous conduits consisting of two elements. The first element defines a needle hub connectable to an open end of a fluid conveying conduit, a needle mounted to the hub, and a base extending from the hub with fingers extending therefrom to define a space through which the needle extends toward an open end, the space being bound by the fingers. The second element is a locking element formed as a collar manually slidable from a retracted position in which a septum can be inserted into the space and penetrated by the needle to locking position flexing the fingers to trap and lock onto the septum.

U.S. Pat. No. 5,376,114, issued on Dec. 27, 1994 to Jarvik, no assignment noted, discloses a cannula pump for temporary cardiac support which is a directly inserted assist pump that is coupled directly to the motor. Thrombus with this pump is prevented by the use of blood-immersed mechanical bearing and the principles of high-flow washing of the junction of the rotary and the stationary parts of the pump.

U.S. Pat. 5,061,256, issued on Oct. 29, 1991 to Wampler and assigned to Johnson and Johnson discloses a cannula with a beveled tip for blind invention of an intravascular blood pump.

U.S. Pat. No. 4,908,012, issued Mar. 13, 1990 to Wampler and assigned to Nimbus Medical, Inc. discloses an implantable continuous delivery ventricle assist system.

BACKGROUND OF THE INVENTION

Heart disease is a major cause of early death throughout the world. One treatment approach is to incorporate an implantable heart assist pump that can work in parallel with the natural heart to provide sufficient blood flow so the person can enjoy a more normal life. In the development of an implantable heart pump there is a continuing need to provide an acceptable coupling for mechanically connecting a rigid or semi-rigid pump to a flexible cannula.

Mechanical couplings for heart pumps involve several serious engineering issues. First, the coupling joint obviously has to be leak-free to prevent blood seepage. Second, the natural tendency of blood to clot at surface discontinuities and interface joints can allow the junction interface to act as a clot initiation site where formed clots could be shed into the blood stream causing serious medical complications. Sometimes, the clot can continue to grow to the point of seriously restricting pump outflow. Third, the joint must maintain its integrity for the literally millions of impulse pressure cycles that, though small, could cause a coupling to work loose. Fourth, it is desirable to make the joint easily separable, for example to accommodate a pump changeout, as well as allow the joint to be made in an operating room to better accommodate the sterilization and cannula treatment processes.

Previously, pumps were joined to a flow cannula by simply inserting the pump tube into the outlet cannula and using a standard hose clamp to secure the tube in place. This was usually adequate because the pumps themselves were relatively short-term, and were mounted external to the body. However, as technical advances resolved problems in the pumps, the "hose clamp" technique has quickly become unsatisfactory, requiring an advance coupling that can be implanted.

Existing couplings simply were not compatible with the medical protocol required for making a fully implantable pump. One of the biggest shortcomings of previous methods is the inherent tendency of blood to form clots at the pump-to-cannula interface joint site once formed, the clots can shed into the blood stream causing other serious medical complications, and occasionally the clots can grow to the point of seriously blocking the blood flow.

SUMMARY OF THE PRESENT INVENTION

The present invention is directed toward a system for coupling a vascular outflow graft or cannula to a heart pump. Specifically, a NASA\DeBakey Heart Pump as disclosed in U.S. Pat. No. 5,527,159.

A pump pipe outlet is provided with an external tapered surface which receives the end of a compressible cannula. For example, cannulae may include flexible polymer tubes or wire reinforced polymer tubes and a cannula should have some flexibility or ability to be compressed. An annular compression ring with a tapered internal bore surface is arranged about the cannula with the tapered internal surface in a facing relationship to the external tapered surface. As the two tapered surfaces are brought axially toward each other, the angle of inclination of the tapered surfaces (i.e., the two tapers have different angles of taper) is converging such that the spacing between the tapered surfaces decreases from one end of the external tapered surface to the other end thereby providing a clamping action of the tapered surfaces on a cannula. The degree of clamping action increases as a function of the length of cannula segment between the tapered surfaces and the disparity between the two taper angles.

In the preferred embodiment, the annular compression ring is disposed within a tubular locking nut which threadedly couples to the pump and provides a compression force for urging the annular ring onto the cannula between the tapered surfaces. The nut has a threaded connection to the pump body. The threaded coupling to the pump body provides a compression force for the annular ring. The annular ring has an annular enclosure space in which excess cannula material from the compression between the tapered surfaces to "bunch up" in the space and serve as an enlarged annular ring segment to assist holding the cannula in place.

The clamped cannula provides a seamless joint connection to the pump pipe outlet where the clamping force is uniformly applied to the cannula because of self alignment of the tapered surfaces. The nut can be easily disconnected to replace the pump if necessary.

DESCRIPTION OF THE PRESENT INVENTION

Figure 1:
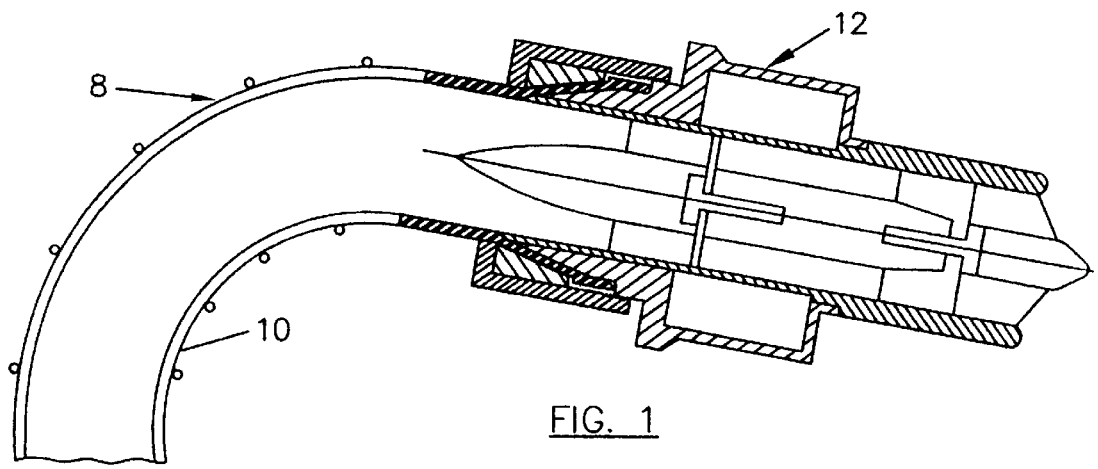
FIG. 1 is a view of a cannula and attached heart pump.

Referring now to FIG. 1, the present invention is illustrated as a coupling system 8 for coupling a vascular outflow graft or cannula 10 to a heart pump 12. Specifically, a NASA\DeBakey Heart Pump as disclosed in U.S. Pat. No. 5,527,159 may be used.

Figure 2:
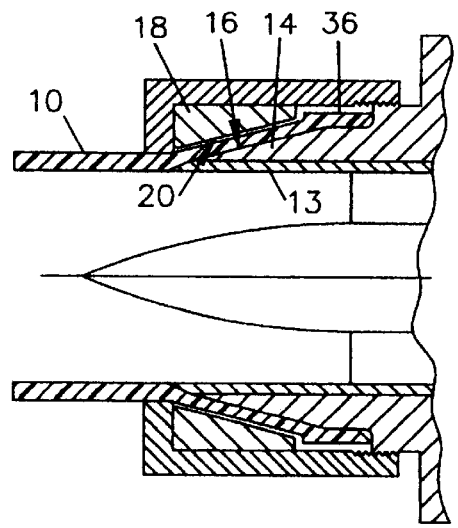
FIG. 2 is an enlarged view in cross section through the coupling of the present invention.
Figure 3:
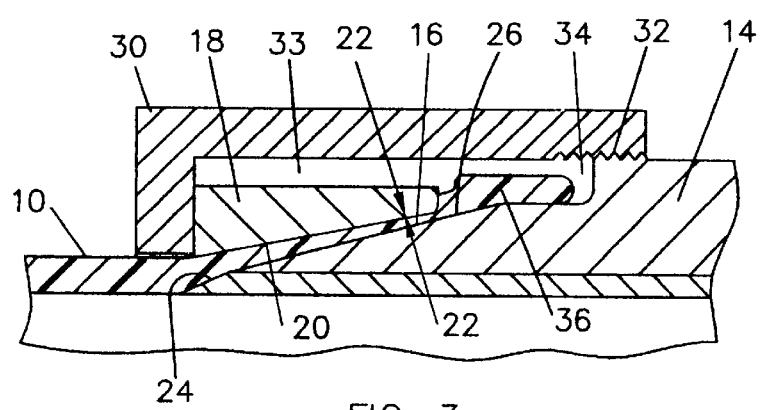
FIG. 3 is a still further enlarged view of one half of the coupling of the present invention.

As seen in FIG. 2, the pump 12 has a tubular pipe outlet 14 which is provided with an external tapered surface 16 extending to a cylindrical internal bore 13. A compressible cannula 10 is mounted over the tapered surface and a cylindrical segment of the pipe outlet. For example, cannulae may include flexible polymer tubes or wire reinforced polymer tubes and a cannula should have some flexibility and ability to be compressed. An annular compression ring 18 with a tapered internal surface 20 is arranged with the tapered internal surface 20 in a facing relationship to the external tapered surface 16. The angle of inclination between the tapered surfaces 16, 20 is converging such that the spacing (arrows 22), FIG. 3, between the tapered surfaces 16, 20 decreases from one end 24 of the external tapered surface to the other end 26 (thereby providing a clamping action of the tapered surface on a cannula 10) as the two tapered surfaces 16 & 18 are moved closer together. This clamping action increases as a function of the length of cannula segment between the tapered surfaces and the disparity between the angles of taper 16, 20.

In the preferred embodiment, the annular ring 18 is disposed within a tubular locking nut 30 which slides over the end of the cannula on the pipe outlet. The nut 30 has a threaded connection to the pump body as shown at 32. The threaded coupling to the pump body provides a force on the annular ring 18 which compresses the cannula between the tapered surfaces. The annular ring 18 centers itself relative to the outlet pipe by virtue of the tapered surfaces. An annular space 33 (FIG. 3) is provided in the nut above the annular ring 18 to permit alignment.

Between the locking nut 30 and the pipe outlet 14 is a second annular space 34 which permits excess cannula material from the compression to "bunch up" in the space 34 and serve as an inflated annular ring segment to assist holding the cannula in place.

The clamped cannula 10 provides a seamless joint connection to the pump pipe outlet 14 where the clamping force is applied uniformly around the cannula because of self alignment of the tapered surfaces 16, 20. The nut 30 can be easily disconnected to replace the pump if necessary.

In the exemplary configuration illustrated, the angle of 30° with respect to a central axis is suitable for the surface 16 and an angle of 28° with respect to a central axis is suitable for the surface 20.

The coupling mechanism can also be used to secure an inflow graft to an inlet or outlet of the pump. This technique can also be used in any number of applications, both in the medical field as well as the non-medical field, where a mechanical coupling is needed to joint flexible conduits to rigid components, and allow the joint to be separable, yet leak free.

It is to be understood that, although the invention is described in terms of a blood pump and outflow cannula for pumping of blood, the invention claimed is not so limited. Accordingly, use of the term "cannula" includes any relatively flexible, compressible tubular material; the term "blood," for the purposes of this application, is generic and also includes any fluid being contained or transported; and the terms "pump," "pipe," "tapered surface," and the like include any relatively harder material object desired to be mechanically attached to a relatively flexible compressible material (cannula).

The coupling solves a serious problem of blood clot formation that can occur at this joint; the clamping force against the pliable cannula material inherently produces a sufficiently smooth transition across the pump\cannula interface to avoid blood clot formations. Additionally, this coupling is separable and reconnectable; is leak free, and compatible with medical implant protocol.

The coupling permits the outflow vascular graft material to be coupled to the metal flow tube of the pump, and at the same time, provide the needed smooth transition between the two materials to avoid causing a thrombus or blood clot formation site. The "second annular space 34" at the upstream end of the tapered surface provides for capturing the "excess" cannula 36 to facilitate assembly and at the same time use the "slightly extruded" material to help lock the cannula in place. This volume variation accommodates slight variations in connector components and cannula geometry, easing manufacturing costs. The ease of disconnecting and reconnecting allows for quicker changeout of a pump, should the need arise. Likewise because the connection is readily separable, it minimizes problems with sterilization as parts where they need different sterilization concepts due to material differences. The slight differential angle between the tapered surface 20 and the tapered surface 16 assure the compression ring 18 remains securely locked into place and remain leak-free.

It will be apparent to those skilled in the art that various changes may be made in the invention without separating from the spirit and scope thereof and, therefore, the invention is not limited by that which is disclosed in the drawings and specifications but only as indicated in the appended claims.

I claim:

1. A connector for attaching a relatively flexible tubular material to a relatively harder tubular material, comprising;

a tubular element having an axis and a terminal segment, said terminal segment having an external surface tapered at a first angle with respect to the axis;

an annular compression member with an internal tapered surface disposed around and generally coaxially with the external tapered surface, said internal tapered surface being tapered at an angle with respect to the axis of said tubular member less than said first angle;

a tubular compressible cannula having a cannula end and being disposed intermediate the external tapered surface and the internal tapered surface, and force applying means for applying a generally axial force to urge the internal tapered surface of said compression member toward said external tapered surface and supply a compressive force to the portion of the cannula between the external tapered surface and the internal tapered surface.

2. The connector as set forth in claim 1, where the compressive force applied to the cannula by the external tapered surface and the internal tapered surface varies as a function of distance along the length of cannula between the external tapered surface and the internal tapered surface.

3. The connector as set forth in claim 2, where said force applying means includes an annular nut member attachable to said tubular element by a threaded connection and engagable with said annular compression member.

4. The connector as set forth in claim 3 wherein said nut member forms a recess with respect to said tubular element, said recess defining an enclosed volumetric space for receiving said cannula end.

5. The connector as set forth in claim 1, where the said first angle at which the external surface is tapered with respect to the axis is about 30°, and the said internal tapered surface is tapered at an angle with respect to the axis of about 28°.

6. The connector as set forth in claim 1, where the compressive force applied to the cannula by the external tapered surface and the internal tapered surface is generally uniformly distributed around the cannula between the external tapered surface and the internal tapered surface for any given distance along the tubular element axis.

* * * * *